(12) United States Patent
Azar

(10) Patent No.: US 7,261,736 B1
(45) Date of Patent: Aug. 28, 2007

(54) VISION PROSTHESIS WITH ARTIFICIAL MUSCLE ACTUATOR

(75) Inventor: Dimitri T. Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 10/895,504

(22) Filed: Jul. 21, 2004

(51) Int. Cl.
*A61F 2/16* (2006.01)

(52) U.S. Cl. .................. 623/6.22; 623/6.27; 351/161; 351/168

(58) Field of Classification Search .............. 623/4.1, 623/6.11, 6.13, 6.15, 6.56, 6.22, 6.24, 6.27, 623/6.37, 24, 25, 14.13; 351/161, 168
See application file for complete search history.

(56) References Cited

U.S. PATENT DOCUMENTS 6,120,538 A * 9/2000 Rizzo et al. ............... 623/6.11
7,122,053 B2 * 10/2006 Esch ......................... 623/6.13
2003/0018383 A1 * 1/2003 Azar ......................... 623/6.22
2003/0028248 A1 * 2/2003 Shahinpoor et al. ......... 623/4.1
2005/0143814 A1 * 6/2005 Esch et al. ................. 623/6.22

OTHER PUBLICATIONS

Steven Ashley, "Artificial Muscles," Scientific American, Oct. 2003, pp. 53-59.

* cited by examiner

*Primary Examiner*—William H. Matthews
(74) *Attorney, Agent, or Firm*—Fish & Richardson P.C.

(57) ABSTRACT

A visual prosthesis includes an artificial muscle configured to deform in response to a focusing signal. The artificial muscle is coupled to at least a portion of an optical system for changing a focal point thereof.

10 Claims, 8 Drawing Sheets

VISION PROSTHESIS WITH ARTIFICIAL MUSCLE ACTUATOR

FIELD OF INVENTION

This invention relates to a vision prosthesis, and in particular, to actuators for assisting in vision accommodation.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances by deforming the lens is referred to as "accommodation."

As a person ages, the lens gradually loses its plasticity. As a result, it becomes increasingly difficult to deform the lens sufficiently to focus on objects at different distances of regard. To compensate for this loss of function, it is necessary to provide different optical corrections for focusing on objects at different distances.

One approach to applying different optical corrections is to carry different pairs of glasses and to swap glasses as the need arises. For example, one might carry reading glasses for reading and a separate pair of distance glasses for driving. This is inconvenient both because of the need to carry more than one pair of glasses and because of the need to swap glasses frequently.

Bifocal lenses assist accommodation by integrating two different optical corrections onto different portions of the same lens. The lower part of the bifocal lens is ground to provide a correction suitable for reading or other close-up work, while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

The concept of a bifocal lens, in which different optical corrections are integrated into the same lens, has been generalized to include trifocal lenses, in which three different optical corrections are integrated into the same lens, and continuous gradient lenses in which a continuum of optical corrections are integrated into the same lens. However, just as in the case of bifocal lenses, optical correction for different ranges of distance using these multifocal lenses relies extensively on relative motion between the pupil and the lens.

Once a lens is implanted in the eye, the lens and the pupil move together as a unit. Thus, no matter how the patient's head is tilted, rays extending between the object-of-regard and the pupil cannot be made to pass through a selected portion of the implanted lens. As a result, multifocal lenses are generally unsuitable for intraocular implantation. Once the lens is implanted into the eye, there can no longer be relative motion between the lens and the pupil.

A lens suitable for intraocular implantation is therefore generally restricted to being a single focus lens. Such a lens can provide optical correction for only a single range of distances. A patient who has had such a lens implanted into the eye may therefore have to continue wearing glasses to provide optical corrections for those distances that are not accommodated by the intraocular lens.

SUMMARY

In one aspect, the invention includes a visual prosthesis having an artificial muscle configured to deform in response to a focusing signal. The artificial muscle is coupled to at least a portion of an optical system for changing a focal point thereof. An optional range finder can be included to provide a focusing signal to an object of regard.

In some embodiments, the artificial muscle is coupled to a natural lens. However, the muscle can also be coupled to an artificial lens. The artificial muscle can be any of a variety of electrically responsive materials. For example, in some embodiments, the artificial muscle includes an electro-active polymer. The artificial muscle can alter the refractive properties of the lens in various ways. For example, in some embodiments, the artificial muscle is configured to cause translation of at least a portion of the optical system in response to the focusing signal. In other embodiments the artificial muscle is configured to deform at least a portion of the optical system in response to the focusing signal.

Deformation of the lens can be achieved by directly or indirectly applying pressure on the lens. For example, in some embodiments, the artificial muscle includes an expandable ring disposed on a periphery of the lens. In others, a plate is coupled to the artificial muscle. The plate is configured to press against at least a portion of the optical system in response to the focusing signal. The plate can be flat plate or a plate having a peripheral portion that contacts a first portion of the optical system and a central portion that defines an expansion cavity between the plate and a second portion of the optical system.

Other embodiments include those in which movement of fluid into or out of the lens causes a change in refractive properties of the lens. For example, the optical system can be a reservoir and a lens in fluid communication with the reservoir. In such embodiments, the artificial muscle can be configured to cause fluid to move between the reservoir and the lens. This can be achieved by positioning the artificial muscle so that it can squeeze the reservoir, thereby pumping fluid from the reservoir to the lens. Alternatively, the artificial muscle is disposed to exert pressure against the lens, thereby pumping fluid from the lens to the reservoir. The artificial muscle can also be integral with the reservoir. In such embodiments, when the artificial muscle contracts, the reservoir squeezes fluid into the lens, thereby changing its refractive properties.

In other embodiments of the visual prosthesis, the optical system includes an artificial muscle that is integral with a lens surface of a lens in the optical system. In these embodiments, contraction of the artificial muscle causes a change in optical properties of the lens. An optional biasing element can be provided for urging the lens surface to deform in a preferred direction.

Additional embodiments include those in which there is local control over the refractive properties of the lens. For example, in some embodiments, the pillars of artificial muscle extend across a lens in the optical system. Each of the pillars is individually addressable. When one of these pillars contracts, it causes deformation of a local portion of the lens.

In other embodiments, the optical system includes a lens having lenslets. In this case, individually addressable artificial muscle elements are each configured to deform the surface of a corresponding lenslet.

Embodiments of the visual prosthesis include those in which the lens is an intraocular lens, or a contact lens, or a lens from a pair of eyeglasses.

These and other features and advantages of the invention will be apparent from the following detailed description and the accompanying figures, in which:

DETAILED DESCRIPTION

Figure 21:
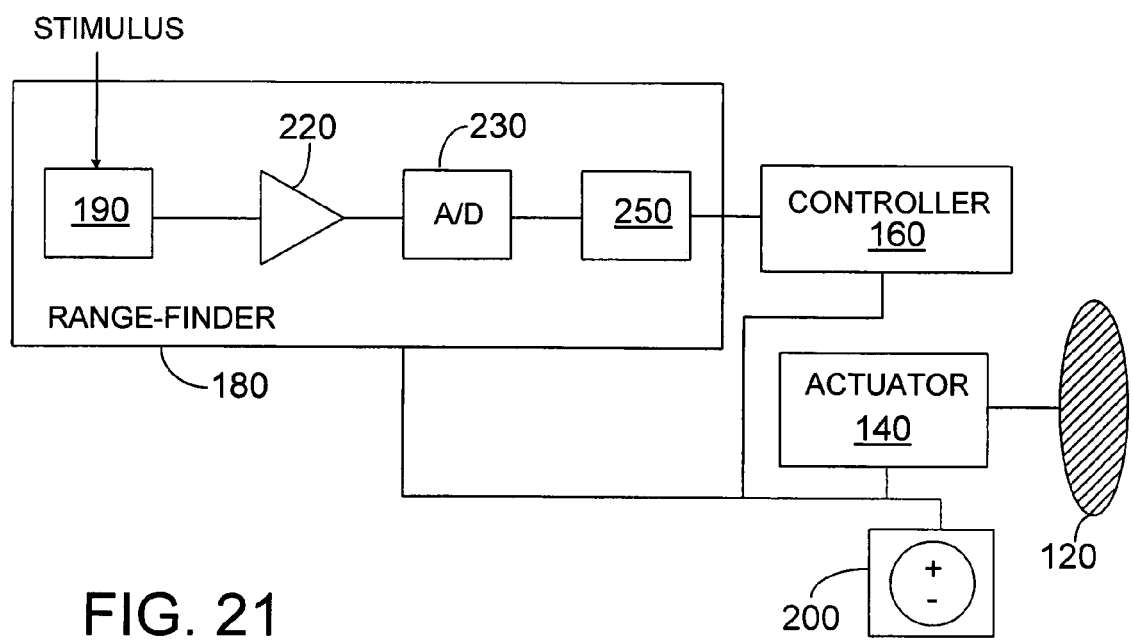
FIG. 21 is a block diagram of a vision prosthesis.

FIG. 21 shows a block diagram of a vision prosthesis 100 having a lens 120 whose index of refraction can be made to vary in response to a focusing signal provided to the lens 120 by an actuator 140. The lens 120 has refractive properties that vary in response to an applied electric field. The actuator 140 includes structures that change shape in response to applied electrical signals. These structures are in mechanical communication with the lens 120.

Throughout this specification, the terms "lens" and "intraocular lens" refer to the prosthetic lens that is part of the vision prosthesis 100. The lens that is an anatomical structure within the eye is referred to as the "natural lens."

The nature of the focusing signal provided by the actuator 140 controls the extent to which the refractive properties of the lens are changed. The actuator 140 generates a focusing signal in response to instructions from a controller 160 in communication with the actuator 140.

The controller 160 is typically a microcontroller having instructions encoded therein. These instructions can be implemented as software or firmware. However, the instructions can also be encoded directly in hardware in, for example, an application-specific integrated circuit. The instructions provided to the microcontroller include instructions for receiving, from a range finder 180, data indicative of the distance to an object-of-regard, and instructions for processing that data to obtain a focusing signal. The focusing signal alters the lens refractive properties to focus an image of the object-of-regard on the retina.

The rangefinder 180 typically includes a transducer 190 for detecting a stimulus from which a range to an object can be inferred. The signal generated by the transducer 190 often requires amplification before it is of sufficient power to provide to the controller 160. Additionally, the signal may require some preliminary signal conditioning. Accordingly, in addition to a transducer 190, the rangefinder 180 includes an amplifier 210 to amplify the signal, an A/D converter 230 to sample the resultant amplified signal, and a digital signal processor 250 to receive the sampled signal. The output of the digital signal processor 250 is provided to the controller 160.

A power source 200 supplies power to the controller 160, the range finder 180, and the actuator 140. A single power source 200 can provide power to all three components. However, the vision prosthesis 100 can also include a separate power source 200 for any combination of those components that require power.

A vision prosthesis thus includes an optical element whose refractive properties can be selectively changed by an actuator in response to a focusing signal. The focusing signal is provided by a controller that determines, on the basis of various cues, how far away an object of regard is. Examples of visual prostheses are described in Azar, U.S. Pat. No. 6,638,304, the contents of which are herein incorporated by reference.

Figure 1:
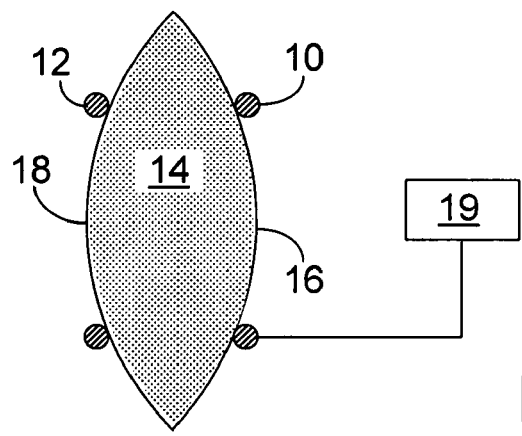
FIGS. 1 and 2 show artificial muscles configured to deform a lens.

One configuration for an actuator, shown in FIG. 1 includes first and second EAP ("electro-active polymer") rings 10, 12 resting on peripheral portions of opposed surfaces 16, 18 of a lens 14. The lens 14 can be an artificial lens, or the patient's natural crystalline lens. In response to a focusing signal provided by a controller 19, the EAP rings 10, 12 deform. This, in turn, causes the lens 14 to deform.

As is well known, a muscle is an anatomical structure that contracts in response to an electrical signal, typically carried by a nerve. The EAP structures described herein can thus be viewed as "artificial muscles" that responds to electrical signals provided by a controller 19. The controller 19, in turn, decides what electrical signals to provide on the basis of a feed back signal. This feedback signal is derived from cues as to how far way an object-of-regard is.

Figure 2:
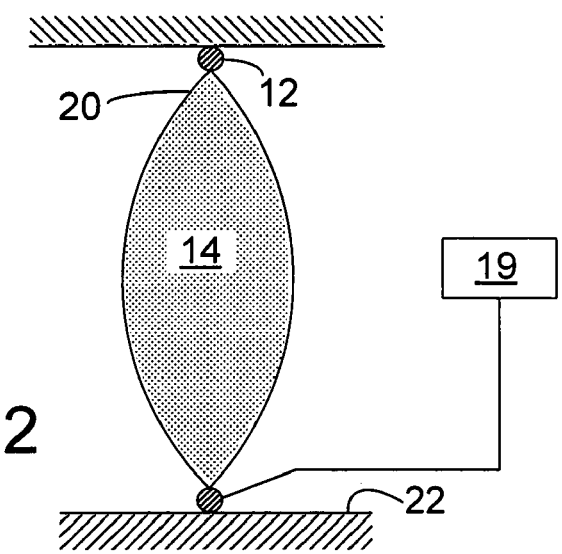

Artificial muscles can be used to change the shape of a lens in other ways. For example, the lens shown in FIG. 2 uses a single EAP ring 12. In this case an inner rim of the EAP ring 12 rests on a haptic 20 of a lens 14, and an outer rim of the EAP ring 12 rests on a stationary surface 22. In response to a focusing signal provided by a controller 19, the ring 12 expands. In so doing, the outer rim braces the ring 12 against the stationary surface 22 and the inner rim presses against the lens 14, causing it to bulge outward.

Figure 3:
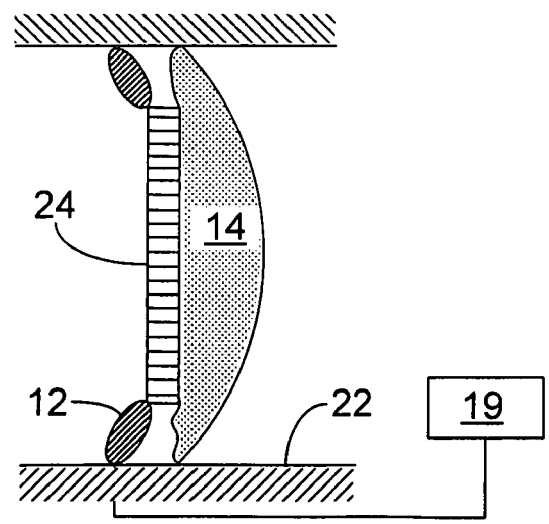
FIGS. 3 and 4 show artificial muscles coupled to translate a plate toward a lens.

Another embodiment, shown in FIG. 3, features a transparent flat plate 24 sandwiched between a lens 14 and an EAP ring 12. In this embodiment, a focusing signal provided by a controller 19 causes the EAP ring 12 to expand, thereby causing the plate 24 to press against, and to thereby flatten, the lens 14.

Figure 4:
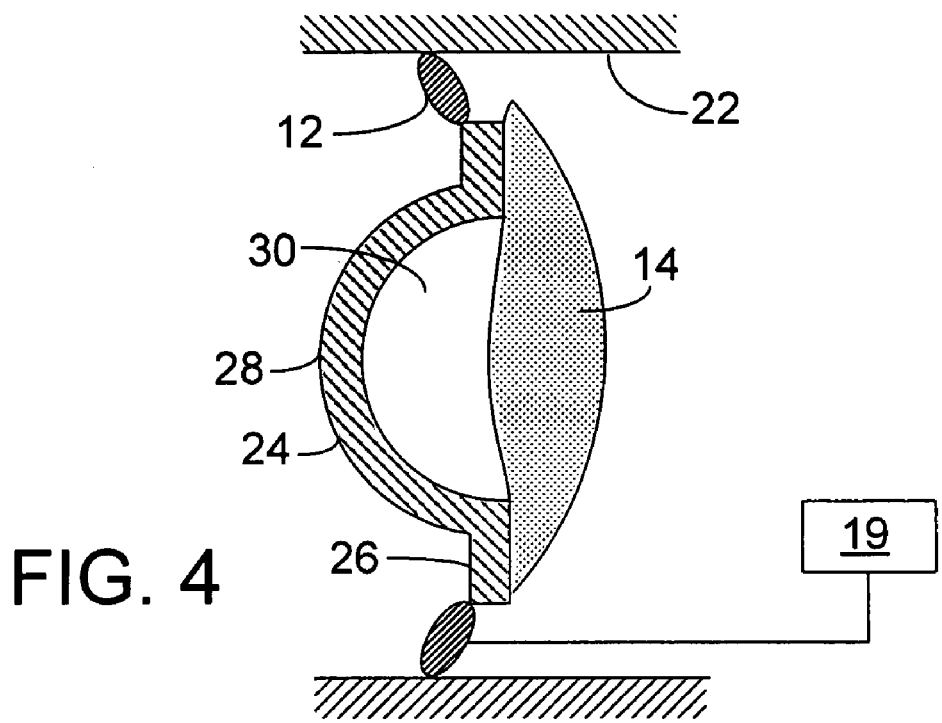

Pressing a plate 24 against the lens 14 can also cause the lens 14 to bulge outwards. For example, the embodiment shown in FIG. 4 features a plate 24 having a peripheral portion 26 that contacts a peripheral portion of a lens 14, and a central portion 28 that bulges outward, away from the lens 14. The lens 14 and the central portion of the plate 24 together define an expansion cavity 30. The peripheral portion 26 of the plate 24 is attached to an inner rim of an EAP ring 12. The outer rim of the EAP ring 12 is attached to a stationary surface 22. In response to a focusing signal provided by a controller 19, the EAP ring 12 expands, thereby forcing the plate 24 toward the lens 14. In this case, the lens 14 bulges outward into the expansion cavity 30.

Additional embodiments feature a reservoir in fluid communication with a lens. In these embodiments, movement of a clear fluid from the reservoir and into the lens causes the lens to bulge outward. Conversely, movement of the fluid from the lens into the reservoir tends to flatten the lens. Various configurations of artificial muscles are available for driving motion of fluid between the reservoir and the lens.

Figure 5:
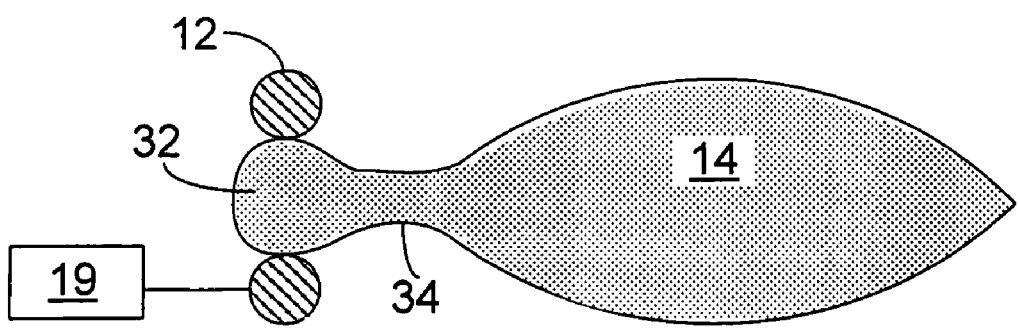
FIGS. 5-7, FIG. 13, and FIG. 14 show artificial muscles configured to pump fluid between a reservoir and a lens.

For example, in FIG. 5, an EAP ring 12 surrounds a reservoir 32 in fluid communication with a lens 14 through a neck 34. In response to a focusing signal provided by a controller 19, the EAP ring 12 expands, thereby squeezing the reservoir 32. This pumps fluid from the reservoir 32 and into the lens 14. When the focusing signal is removed, the reservoir 32 expands, drawing fluid out of the lens 14 and back into itself.

Figure 6:
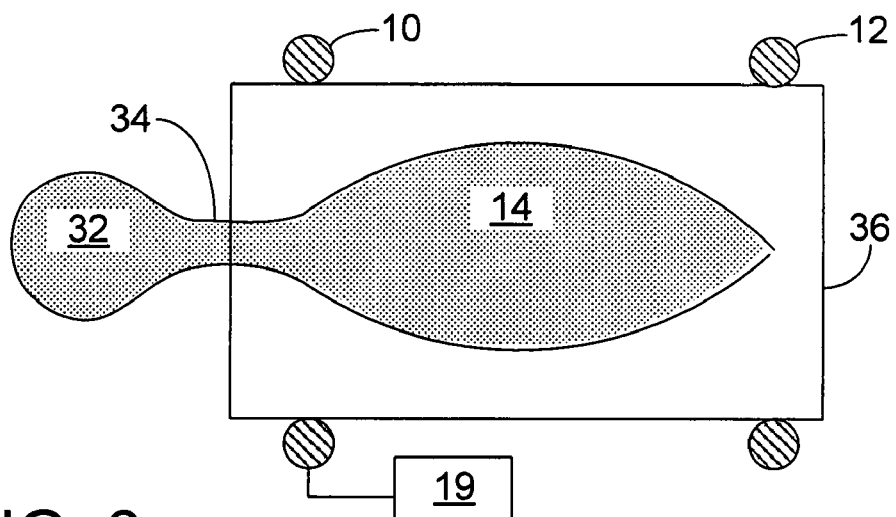

In another embodiment, shown in FIG. 6, a transparent jacket 36 surrounds the lens 14, but not the reservoir 32. A pair of EAP rings 10, 12 is disposed on opposed outer surfaces of the jacket 36. In this embodiment, a focusing signal provided by a controller 19 causes the EAP rings 10, 12 to expand. This exerts a pressure against the jacket 36. The jacket 36 transmits the pressure to the lens 14, thereby pumping fluid from the lens 14, through a neck 34, and into the reservoir 32.

Figure 7:
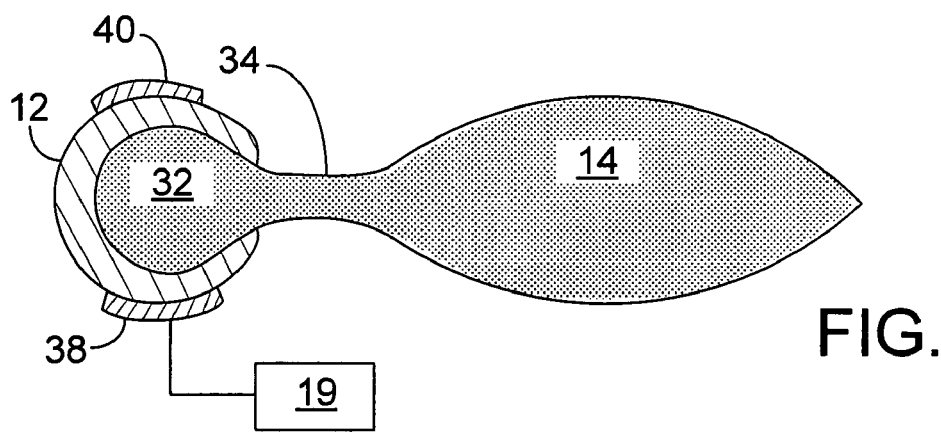

FIG. 7 shows an embodiment in which the reservoir 32 itself is made of an EAP 12. When a voltage is applied across flexible electrodes 38, 40 on opposite sides of the EAP reservoir 32, the reservoir 32 changes its shape so as to squeeze fluid within the reservoir 32 through a neck 34 and into a lens 14. Removing the voltage causes the reservoir 32 to relax and expand, thereby drawing fluid out of the lens 14 and into the reservoir 32. In this embodiment, the reservoir 32 functions essentially as a single-chamber artificial heart.

In the embodiments discussed thus far, artificial muscles are used to cause a shape change in a lens. However, there also exist embodiments in which an artificial muscle causes translation, rather then deformation, of a lens.

Figure 8:
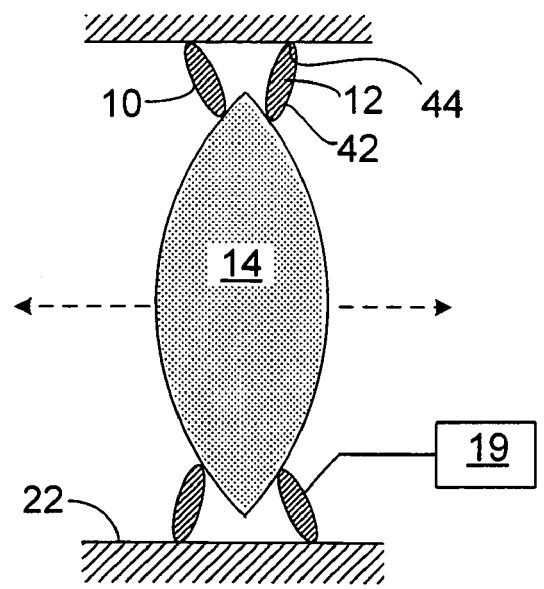
FIGS. 8-10 show artificial muscles configured to translate a lens.

For example, in FIG. 8, first and second EAP rings 10, 12 have inner rims 42 attached to a periphery of a lens 14 and outer rims 44 anchored to a stationary surface 22. The outer rims 44 of the EAP rings 10, 12 are longitudinally displaced from the inner ring 42 thereof. As a result, when voltages are selectively applied to the EAP rings 10, 12, the lens 14 translates longitudinally. For example, a voltage that causes contraction of the first ring 10 and relaxation of the second ring 12 will translate the lens 14 forward, while the converse will translate the lens 14 backward.

A disadvantage of the arrangement shown in FIG. 8 is that a great deal of translation is often necessary to effect a significant change in the patient's vision. This disadvantage is addressed by the embodiment of FIG. 9, in which a translating lens 14 like that shown in FIG. 8 is mounted within a frame 46 that includes one or more stationary optical elements 48.

Figure 9:
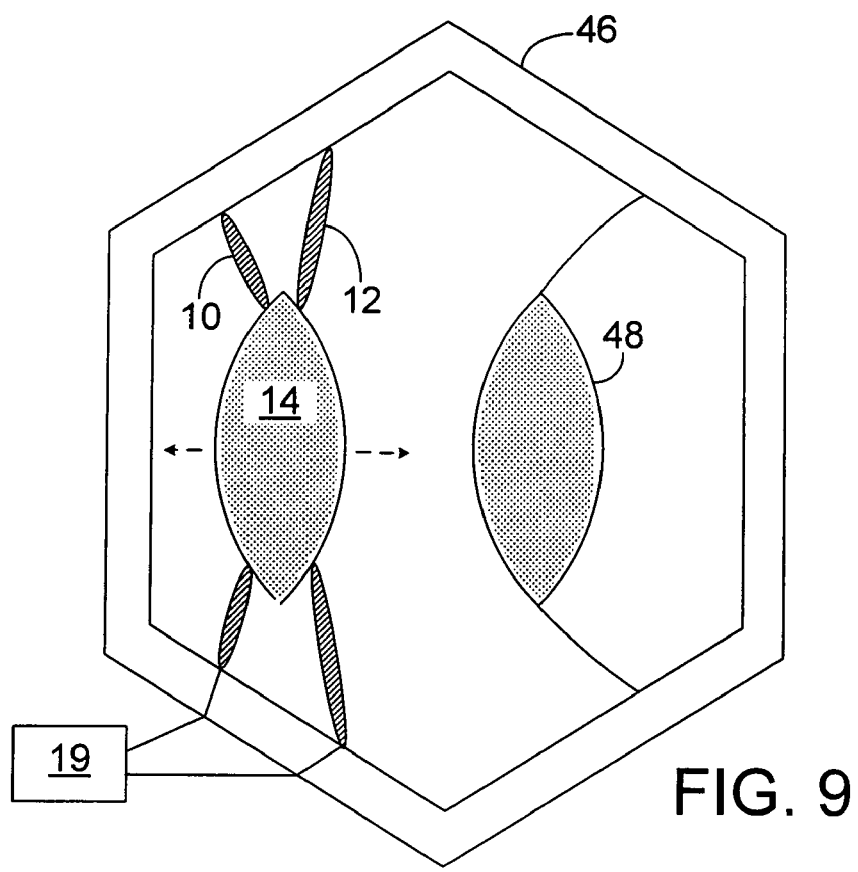
Figure 10:
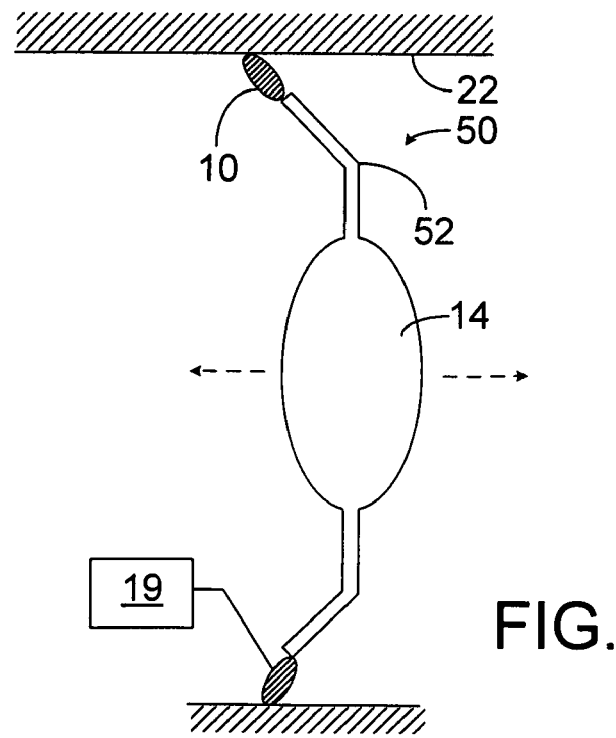

A variety of ways are available for configuring artificial muscles to move a lens 14 in addition to those already shown in FIGS. 8 and 9. For example, in FIG. 10, the haptic 50 of the lens 14 includes a genue 52 that buckles in a preferred direction. An outer rim of the haptic 50 is coupled to an inner rim of an EAP ring 10, the outer rim of which is fixed to a stationary surface 22. In this embodiment, expansion of the EAP ring 10 causes the genue 52 to buckle, thereby shifting the lens 14 in the axial direction.

Figure 11:
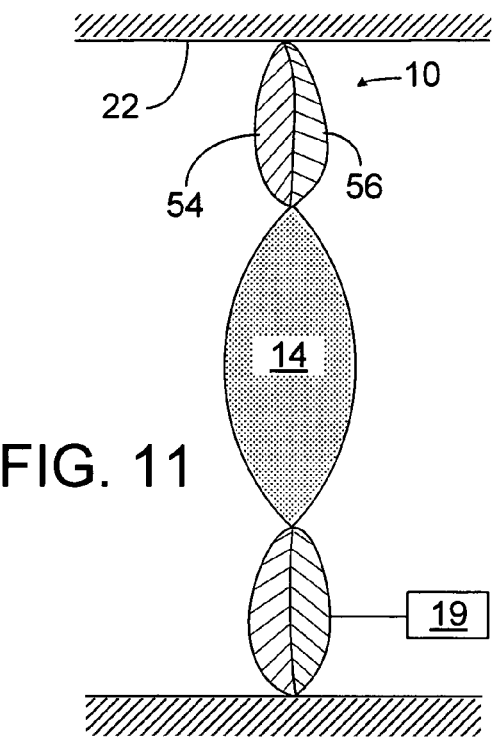
FIG. 11 shows an artificial muscle made with two different electro-active polymers.

Another configuration for an EAP ring 10, shown in FIG. 11, makes use of the same principle as a bimetallic strip in a thermostat. In this configuration, the EAP ring 10 has two different layers 54, 56, each made of a different type EAP. In response to a voltage, both EAP layers 54, 56 will expand by different amounts, thereby causing the EAP ring 10 to bend in a preferred direction.

Figure 12:
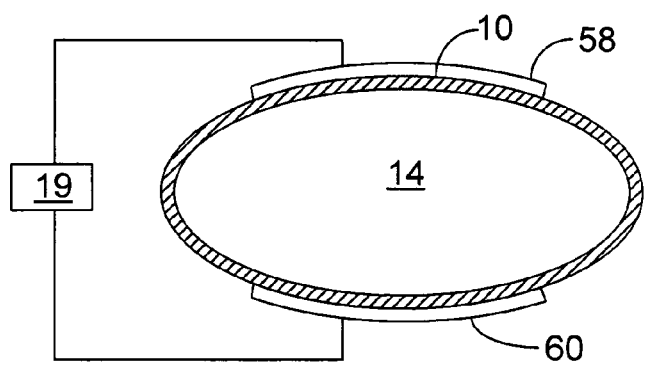
FIG. 12 shows a lens having an artificial muscle integral with a lens surface thereof.

In another embodiment, shown in FIG. 12, the lens 14 can be made of an optically transmissive EAP 10. In this case, the front and rear surfaces of the lens 14 can be coated with flexible, optically transmissive electrodes 58, 60. In response to a voltage applied between the electrodes 58, 60, the lens 14 changes shape.

A variation of the embodiment shown in FIG. 7 is one in which it is the lens 14 rather than the reservoir 32 that is made an EAP. Referring to FIG. 13, a reservoir 32 is again placed in fluid communication with a lens 14 though a neck 34. At least one surface 10 of the lens 14 is made of an EAP that expands in response to voltage applied between a pair of electrodes 58, 60.

Figure 13:
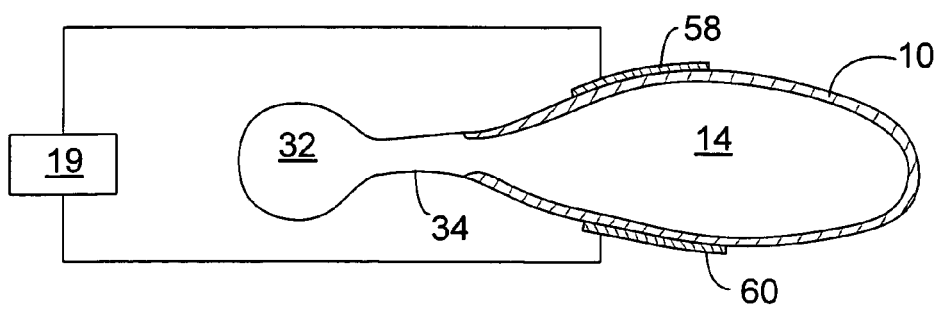
Figure 14:
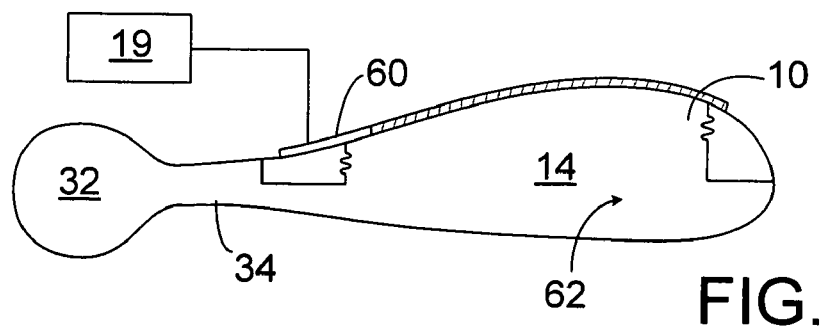
Figure 15:
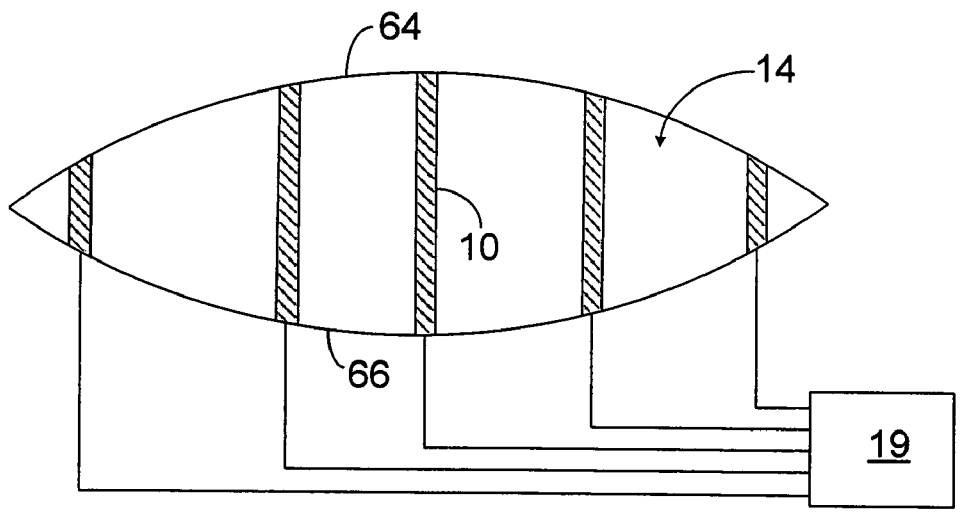
FIG. 15 shows a lens having internal artificial muscles configured to locally deform its surface.

Another embodiment, shown in FIG. 14, includes the structures shown in the embodiment of FIG. 13 but with the addition of a biasing structure 62 to urge deformation of the EAP surfaces in a preferred direction. The biasing structure 62 can include springs, as shown, or foam blocks that extend from a midline of the lens 14 toward the EAP lens surface 10.

Figure 16:
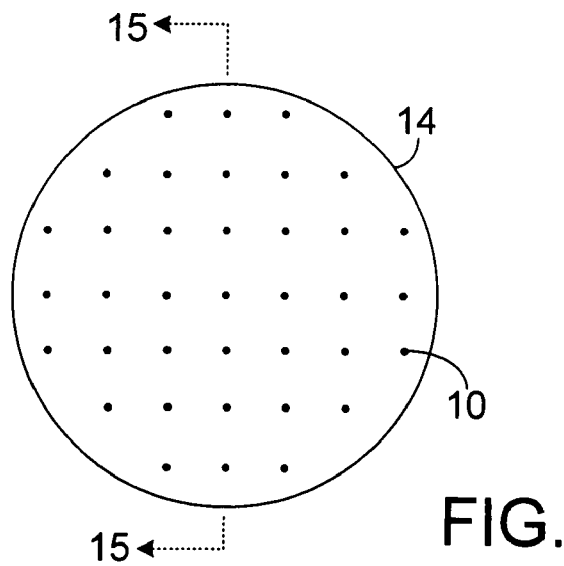
FIGS. 16-17 show exemplary layouts for the locations of artificial muscles in the lens shown in FIG. 15.
Figure 17:
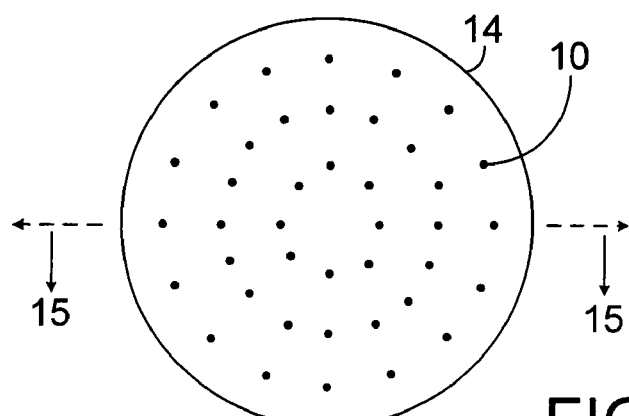

In the embodiments presented thus far, artificial muscles alter the shape of the entire lens. However, in other embodiments, artificial muscles can be used to locally alter the shapes of selected portions of a lens 14 and to do so in different ways. For example, in FIG. 16 individually addressable pillars 10 made of an EAP are distributed throughout a lens 14 in a grid. The grid can be a rectangular grid (as shown in FIG. 16) or a grid of concentric circles (as shown in FIG. 17). Each pillar 10 extends across the lens 14, with the ends of the pillars 10 being attached to opposed surfaces 64, 66 thereof. In response to a focusing signal, a particular pillar 10 will change its length. This, in turn, will change the thickness of the lens 14 in a region local to that pillar 10. Since the pillars 10 are individually addressable, the controller 19 can vary the shape of the lens 14 in an essentially arbitrary way.

Figure 18:
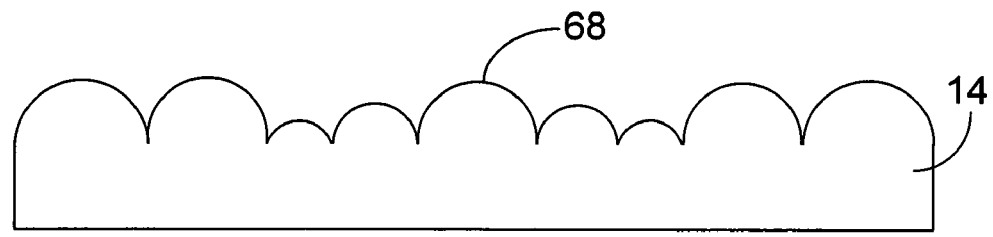
FIGS. 18-19 are cross-section and planar views respectively of a lens having lenslets that can be selectively deformed by artificial muscles.
Figure 19:
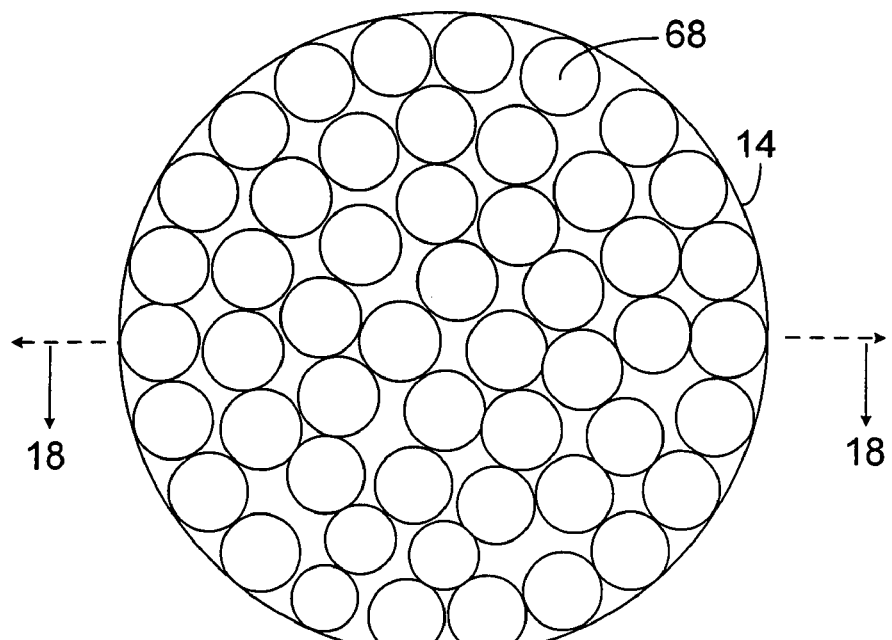
Figure 20:
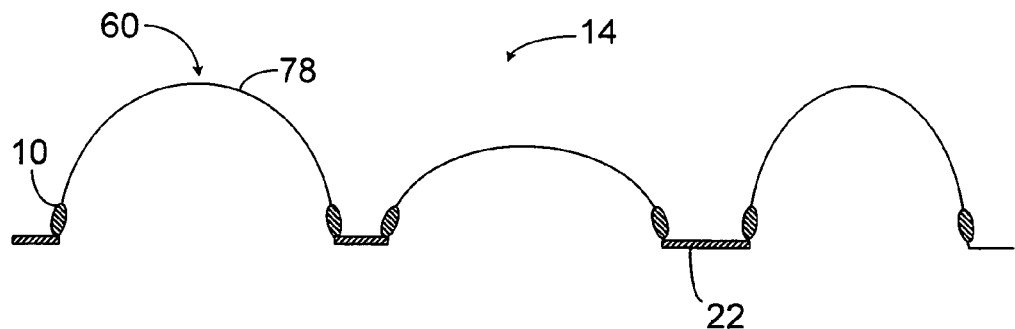
FIG. 20 is a close-up view of a lenslet from FIG. 18.

Another way to provide localized control over the shape of a lens 14 is to make the lens 14 from a honeycomb of lenslets 68 as shown in FIGS. 18 and 19. Each lenslet 68 has a flexible surface 78 that is coupled to a rigid surface 22 by an individually addressable EAP ring 10.

In response to an applied voltage, the EAP material in the ring 10 expands, thereby reducing the ring's inner diameter. This causes the upper surface 78 to flatten, which in turn locally changes the curvature of the lens 14.

A variety of EAP materials can be used in the embodiments described herein. One class of materials includes piezoelectric materials. These materials offer the advantage of high actuation pressures (ranging from 7 to 70 kilopascals meter$^3$/kg). However, piezoelectric materials undergo only a limited strain of, which in many cases is less than 1%.

Another class of EAPs includes ionic EAPs, such as polymer gels, ionomeric polymer-metal composites, conductive polymers, and carbon nanotubes. These materials undergo strain even at low voltages (less than or equal to approximately 9 volts). A disadvantage of ionic EAPs is that they are best kept wet, and hence sealed within a flexible coating.

Another class of EAPs for use in a vision prosthesis includes electronic EAPs, such as ferroelectric polymers, electrets, dielectric elastomers, and electrostictive graft elastomers. These materials require high voltages for actuation.

However they can deliver considerable force in a short time. Unlike the ionic EAPs, these materials can function without a protective coating and require only a minimal current to maintain their position.

Vision prosthesis that include EAP actuators can be used in a variety of applications. These include intraocular lenses, contact lenses, and spectacle lenses. These applications are fully described in U.S. Pat. No. 6,638,304.

Having described the invention and preferred embodiments thereof, I claim:

1. A visual prosthesis comprising pillars extending across a lens in an optical system, each of the pillars being individually addressable, whereby contraction of a pillar causes deformation of a local portion of the lens, wherein each pillar comprises an artificial muscle that deforms in response to an electrical focusing signal applied thereto, the focusing signal being indicative of a range to an object of regard, the artificial muscle being coupled to at least a portion of an optical system for changing a focal point thereof.

2. The visual prosthesis of claim 1, further comprising a rangefinder for providing the focusing signal.

3. The visual prosthesis of claim 1, further comprising a lens coupled to the artificial muscle.

4. The visual prosthesis of claim 1, wherein the artificial muscle comprises an electro-active polymer that deforms in response to electrical stimulation.

5. The visual prosthesis of claim 1, wherein the artificial muscle is configured to cause translation of at least a portion of the optical system in response to the focusing signal.

6. The visual prosthesis of claim 1, wherein the artificial muscle is configured to deform at least a portion of the optical system in response to the focusing signal.

7. The visual prosthesis of claim 1, wherein the optical system comprises a lens having a lens surface, and wherein the artificial muscle is integral with the lens surface, whereby contraction of the artificial muscle causes a change in optical properties of the lens.

8. The visual prosthesis of claim 3, wherein the lens comprises an intraocular lens.

9. The visual prosthesis of claim 3, wherein the lens comprises a contact lens.

10. The visual prosthesis of claim 3, wherein the lens comprises an eyeglass lens.

* * * * *